United States Patent [19]

Gemma, Jr. et al.

[11] Patent Number: 5,860,517
[45] Date of Patent: *Jan. 19, 1999

[54] UNIVERSAL SUTURE DISPENSER BOX

[75] Inventors: Edward A. Gemma, Jr., Milford; David Viselli, Shelton; Terry L. Ritchie, Guilford, all of Conn.

[73] Assignee: United States Surgical Corporation, Norwalk, Conn.

[*] Notice: This patent issued on a continued prosecution application filed under 37 CFR 1.53(d), and is subject to the twenty year patent term provisions of 35 U.S.C. 154(a)(2).

[21] Appl. No.: 680,947

[22] Filed: Jul. 16, 1996

[51] Int. Cl.⁶ .............................. A61B 17/06; B65D 5/72
[52] U.S. Cl. .................... 206/63.3; 206/499; 221/305; 229/122.1
[58] Field of Search .................. 206/63.3, 499; 229/122.1; 211/266, 281, 197, 256; 221/305, 306

[56] References Cited

U.S. PATENT DOCUMENTS

| | | |
|---|---|---|
| D. 221,427 | 8/1971 | Savettiere et al. . |
| D. 224,692 | 8/1972 | Gray . |
| D. 232,677 | 9/1974 | Schotland . |
| D. 260,955 | 9/1981 | Schuler et al. . |
| 902,347 | 10/1908 | Tillinghast . |
| 1,119,213 | 12/1914 | Abt . |
| 1,823,572 | 9/1931 | Reed . |
| 1,973,237 | 9/1934 | Vilas . |
| 1,986,101 | 1/1935 | Brodsky .......................... 229/122.1 X |
| 2,002,485 | 5/1935 | Alfred . |
| 2,005,924 | 6/1935 | Wilson ............................ 229/122.1 X |
| 2,577,862 | 12/1951 | Shaw, Jr. . |
| 2,755,922 | 7/1956 | Volckening . |
| 2,767,832 | 10/1956 | Silberman . |
| 3,014,634 | 12/1961 | Humphrey et al. . |
| 3,156,378 | 11/1964 | Bua . |
| 3,160,342 | 12/1964 | Murdock et al. . |
| 3,356,279 | 12/1967 | Root . |
| 3,568,883 | 3/1971 | Reynolds . |
| 3,580,472 | 5/1971 | Stawski . |
| 3,586,206 | 6/1971 | Gilmore et al. . |
| 4,148,413 | 4/1979 | Immordino . |
| 4,170,325 | 10/1979 | Pawlowski et al. . |
| 4,186,866 | 2/1980 | Zicko ............................... 229/122.1 X |
| 4,215,777 | 8/1980 | Strickland . |
| 4,396,143 | 8/1983 | Killy . |
| 4,405,044 | 9/1983 | Flower et al. . |
| 4,458,814 | 7/1984 | Meschi . |
| 4,497,432 | 2/1985 | Milia . |
| 4,566,607 | 1/1986 | Smith . |
| 5,282,533 | 2/1994 | Holzwarth et al. . |
| 5,284,293 | 2/1994 | Alpern et al. . |
| 5,458,272 | 10/1995 | Ward-Weber ....................... 229/122.1 |
| 5,542,539 | 8/1996 | Early ............................. 206/499 |

FOREIGN PATENT DOCUMENTS

| | | | |
|---|---|---|---|
| 2458480 | 2/1981 | France ........................... 229/122.1 |

*Primary Examiner*—Bryon P. Gehman

[57] ABSTRACT

A dispenser box for suture packages includes an outer casing and drawer portion slidably disposed within the outer casing. The dispenser preferably includes at least two access portals for withdrawal of the suture packages. A first access portal allows the suture packages to be withdrawn in accordance with the U.S. preferred mode, wherein the dispenser box disposed so that the suture packages are stacked in a vertical array and withdrawn horizontally. A second access portal allows the suture packages to be withdrawn in accordance with the European preferred mode, wherein the suture packages are stacked in a horizontal array and are withdrawn vertically.

21 Claims, 14 Drawing Sheets

UNIVERSAL SUTURE DISPENSER BOX

BACKGROUND

1. Technical Field

The container disclosed herein relates to a dispensing box for surgical suture packages. More specifically, the suture dispensing box is configured to be used in both the U.S. preferred mode wherein the box is vertically disposed, and in the European preferred mode, wherein the box or a portion thereof is disposed horizontally.

2. Background of the Art

Modern surgical procedures draw upon a wide variety of types and sizes of surgical sutures. These sutures are usually contained in individual retainers or foil laminate envelopes wherein the suture is wound, for example, in a figure eight type pattern, or coil. Indicia indicating the size and type of the suture are typically printed on the enclosure envelopes to facilitate identification.

Dispensing boxes for such suture packages are known in the art. As shown In FIG. 1, the preferred format for dispensing boxes in the United States is to have the longer side of the box 2 disposed vertically. Suture packages 50 are retrieved horizontally from the bottom of the vertical stack of suture packages by grasping a shorter side of the generally rectangular suture package. As suture packages are withdrawn, the stack drops down to reposition other packages for retrieval.

The preferred European format, however, is with the longer side of the dispenser 2a and the stack of suture packages 50 disposed horizontally, as shown in FIG. 2. The dispenser 2a acts like a drawer, the suture packages being withdrawn vertically from the dispensing box 2a by grasping the longer side of the generally rectangular suture package. A typical operating room has suture box shelving or racks configured to accommodate either the U.S. or European boxes.

Because the U.S. and European dispensing boxes have different configurations, manufacturers currently provide separate boxes for each market. As such, two separate manufacturing, labeling and inventory systems must be maintained. What is needed is a dispensing box that can be used in both the U.S. preferred mode and the European preferred mode. Such a universal dispenser would eliminate the need for separate box constructions for different markets, providing both economy of manufacture and flexibility of use.

SUMMARY

A universal suture dispenser box is provided herein. The universal suture dispenser is a container for holding a plurality of suture packages in a stacked array. In a preferred embodiment, the container has first and second adjacent sides, the suture packages being individually oriented perpendicular to the first side and parallel to the second side. The container has first and second access portals for withdrawal of the suture packages from the stacked array. The first access portal permits the suture packages to be withdrawn from the container in a line of direction perpendicular to the first side and parallel to the second side. The second access portal permits the sutures to be withdrawn from the container in a line of direction parallel to both the first and second sides. In a most preferred embodiment, the universal suture package dispenser includes an outer casing and a drawer portion slidably disposed within the outer casing. The drawer portion has a storage space for holding the stacked array of suture packages.

The outer casing preferably includes a first side, a second side foldably connected to the first side along an edge thereof, a third side foldably connected to the second side on an edge of the second side opposite to the edge at which the first side is foldably connected, a fourth side foldably connected to the third side along an edge of the third side opposite to that at which the second side is connected, and a fifth side foldably connected to the third side, the aforementioned sides forming at least a partial enclosure defining an interior space and having an open end. The drawer portion includes first, second, third, fourth, fifth, sixth, and seventh panels, the first and third panels being foldably connected to the second panel along adjacent edges thereof, the fifth and fourth panels being foldably connected to the sixth panel along adjacent edges of the third panel, and the fifth and seventh panels being foldably connected to the sixth panel along respective adjacent edges of the sixth panel. The fifth and second panels are foldably connected to opposite edges of the third panel, and the sixth and third panels are foldably connected to opposite edges of the fifth panel.

The universal suture package dispenser can be positioned vertically for dispensing suture packages in the U.S. preferred mode, or horizontally, wherein the suture packages can be withdrawn in the European preferred mode. Preferably, a spacer panel is included to conform the dimensions, of the dispensing box to those of conventional box shelving.

DETAILED DESCRIPTION OF THE DRAWINGS

DETAILED DESCRIPTION OF PREFERRED EMBODIMENTS

With reference to FIGS. 3–11, a preferred universal suture dispenser 10 is described herein. Universal suture dispenser 10 includes an outer casing 100 having a folded blank defining an interior space, and a drawer portion 200 slidably disposed within the interior space of the outer casing. Individual suture packages are preferably stacked in a single array within the drawer portion. The suture packages are typically of a rectangular, planar configuration and are stacked such that the planes are parallel to each other. The stack can be positioned vertically, as in FIG. 3, or horizontally, as in FIG. 4. The suture dispenser can be fabricated from paperboard, cardboard stock, plastic sheet material or other material suitable for the purposes described herein.

Figure 3:
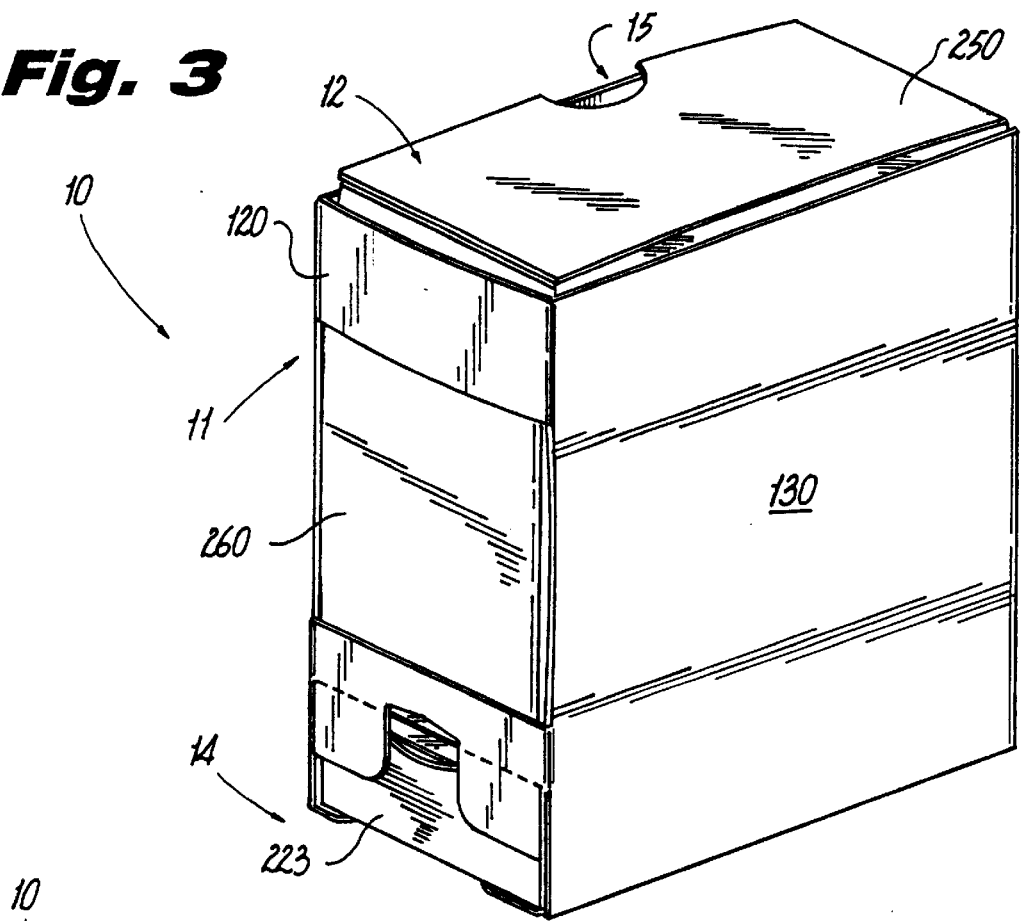
FIG. 3 is a perspective view of a preferred universal dispenser box described herein positioned in a vertical orientation.
Figure 4:
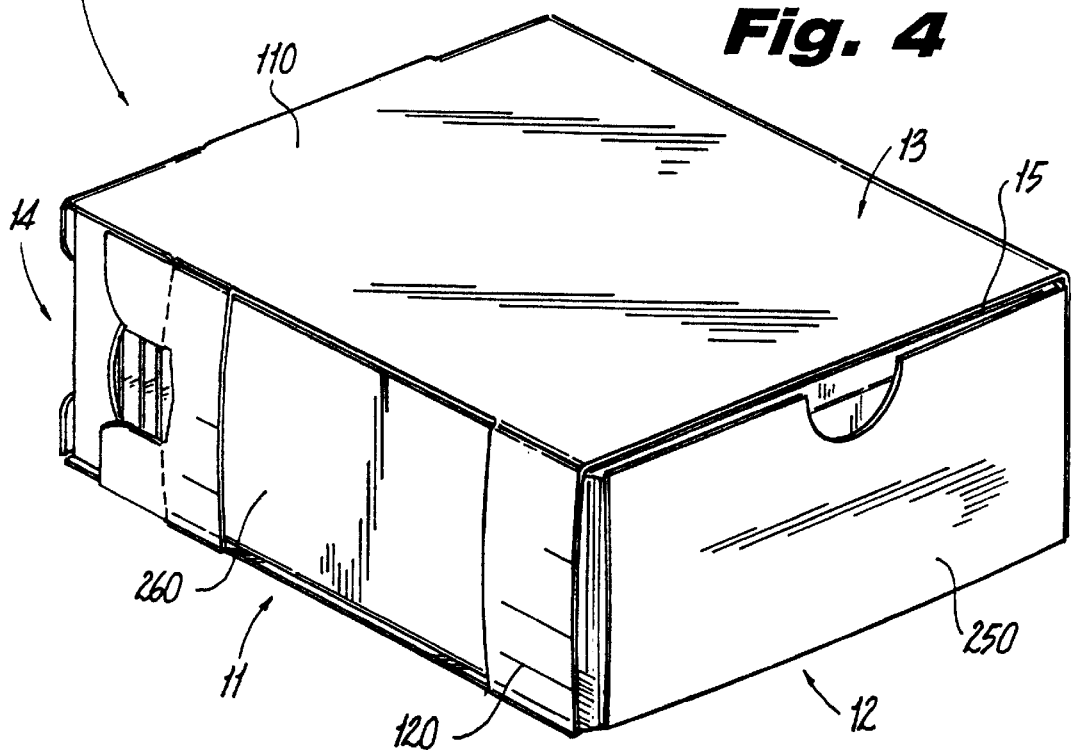
FIG. 4 is a perspective view of the universal dispenser box of FIG. 3 positioned in a horizontal orientation.

Referring now to FIG. 3, universal suture dispenser 10 is illustrated in a vertical position as favored in the United States. FIG. 4 illustrates the universal suture dispenser 10 positioned in the European preferred horizontal orientation.

Figure 5:
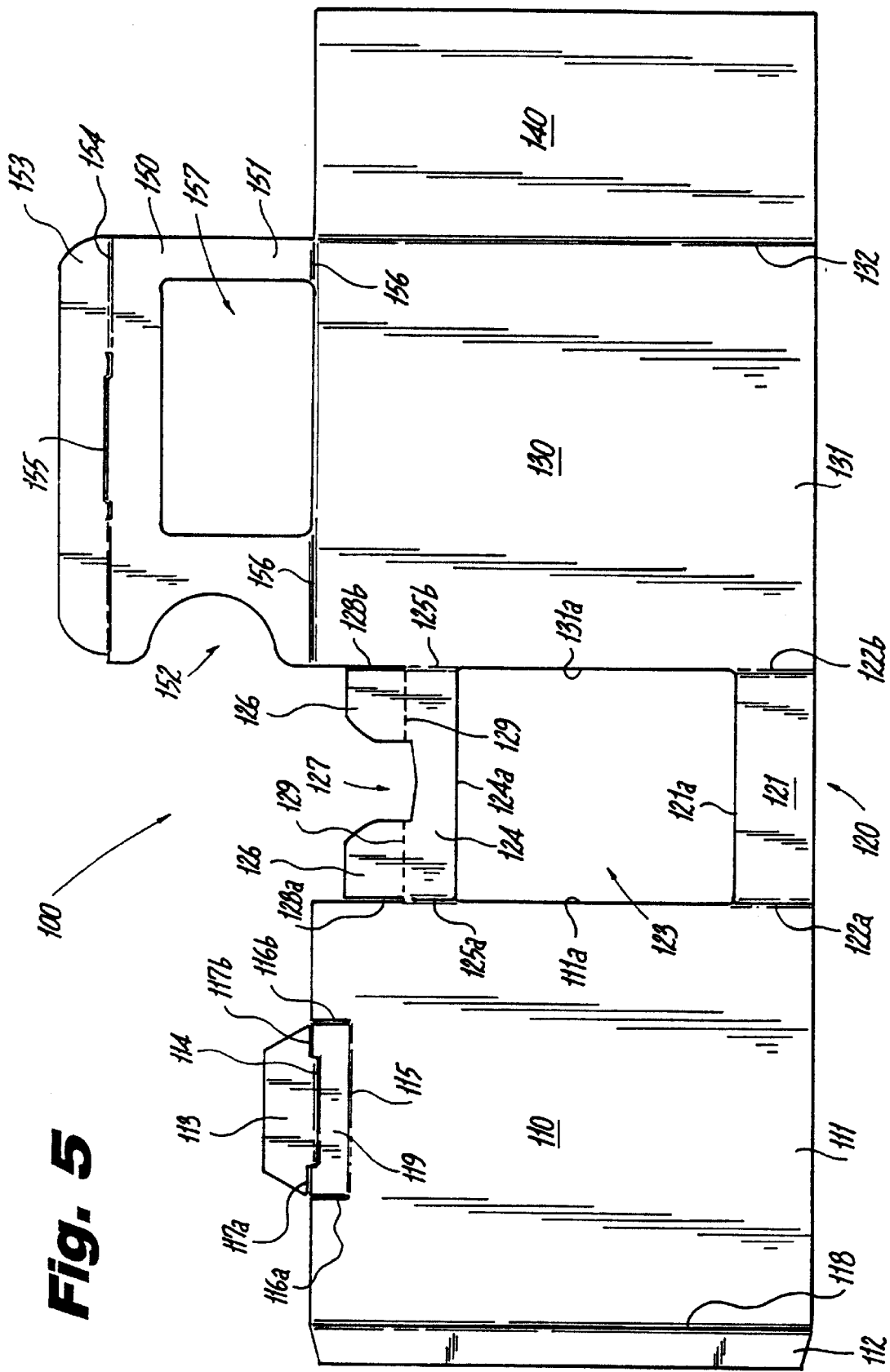
FIG. 5 is a plan view of the blank used to make the outer case of the universal dispenser shown in FIG. 3.

Referring now to FIG. 5, the blank from which the outer casing 100 is made is shown unfolded. The blank has five main panels which correspond to sides of the outer casing. Each of the panels is a flat sheet of suitable material.

A first panel 110 has a body portion 111 to which flap 112 is attached along fold line 118. Tab 113 is adapted for insertion into slot 155 (discussed below) and is attached to bendable portion 119 along fold line 114. Bendable portion 119 is at least partially defined by slots 116a and 116b, and is attached to body portion 111 along fold line 115. Slots 117a and 117b between tab 113 and bendable portion 119 facilitate the bending of tab 113 relative to the bendable portion 119 and help to prevent inadvertent withdrawal of tab 113 from slot 155 after they have been fully engaged.

A second panel 120 has a first strip portion 121 extending between panels 110 and 130 and being foldably connected thereto along fold lines 122a and 122b, respectively. A second strip portion 124 extends between panels 110 and 130 and is foldably connected thereto along fold lines 125a and 125b. Edges 111a of the panel 110, 131a of panel 130, 124a of strip 124, and 121a of strip 121 define a window 123. Window 123 enables the operating room personnel or other user to see identifying indicia printed on the outer side of panel 260 of the drawer portion 200 (FIG. 7) when the dispenser is assembled.

Bendable tabs 126 are attached to strip portion 124 along fold lines 129 and are at least partially defined by slits 128a and 128b. Finger slot 127 provides access to grasp the suture package with one's fingers (usually forefinger and thumb).

A third panel 130 includes a body portion 131 attached to first and second strip portions 121 and 124 along fold lines 122b and 125b, respectively, and further is attached to panel 140 along fold line 132.

A fourth panel 150 includes a body portion 151 attached to panel 130 along fold line 156 and also includes a window 157 for permitting the operating room personnel or other user to read identifying indicia on the outer surface of panel 220 of the drawer portion 200.

A fifth panel 150 also preferably includes an arcuate cut out portion 152 to facilitate grasping of the suture package for withdrawal. Tab 153 is bendably attached to body portion 151 along fold line 154. Slot 155 is disposed along fold line 154 and is adapted to receive tab 113 of the first panel when the panels are folded together to form the outer casing.

Figure 6:
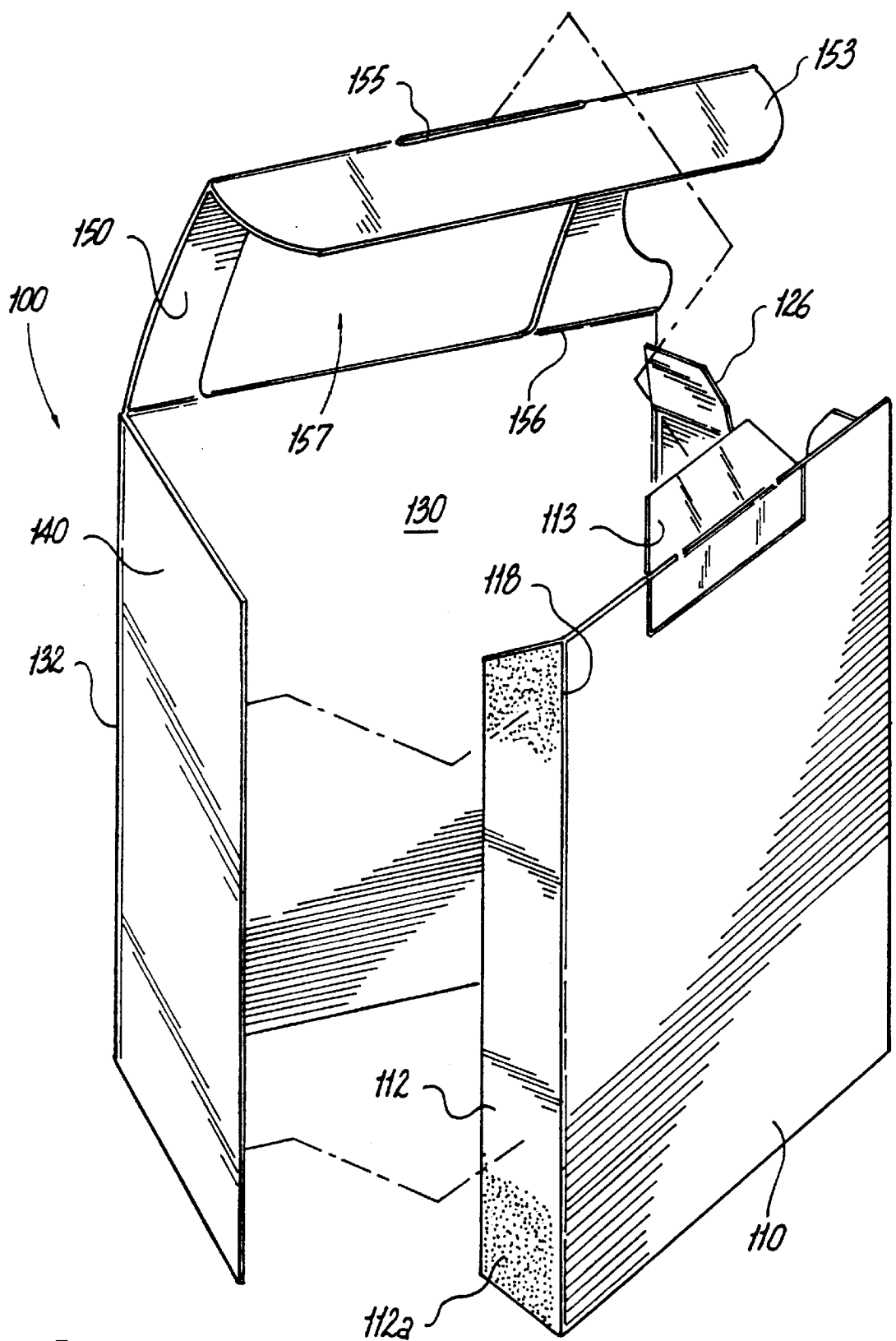
FIG. 6 is a perspective view illustrating the folding and assembly of the blank of FIG. 5 to form the outer case.

Referring now to FIG. 6, this folding operation is illustrated. Panels 110, 120, 130, 140, and 150 are folded inward along fold lines 122a, 125a, 122b, 125b, 132, and 156 to form a box-like structure. Tab 112 includes a gummed adhesive surface 112a adapted to abut an inner surface portion of panel 140 and to adhere thereto. Panel 150 is folded with tab 153 tucked inside panel 110 with tab 113 being inserted through slot 155 to lock the panels and secure the enclosure. The outer casing thus formed is prepared to receive the drawer portion 200.

Figure 7:
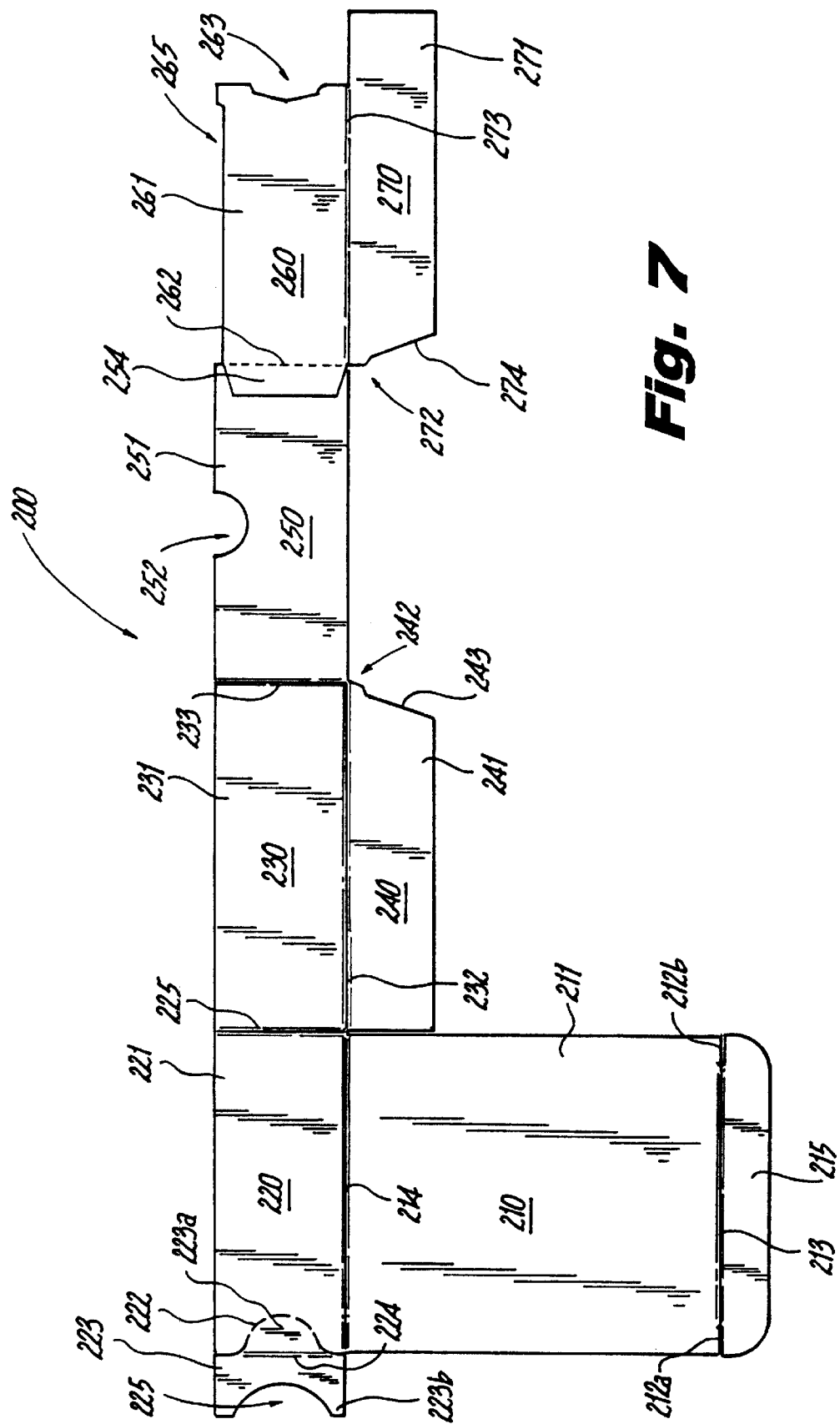
FIG. 7 is a plan view of a blank used to make the drawer portion of the dispensing box shown in FIG. 3.

Drawer portion 200 is adapted to provide a storage space in which the suture packages are stacked. Referring to FIG. 7, as seen in unfolded plan view, the blank from which the draw portion is folded includes several foldably connected panels.

A first panel 210 includes a body portion 211. Flap 215 is attached to body portion 211 along fold line 213. Slits 212a and 212b facilitate folding of tab 215 and its retention in the tucked-in configuration by panels 240 and 270, as discussed below. Panel 210 is foldably attached to panel 220 along fold line 214.

A second panel 220 includes body portion 221 connected along one edge to panel 210 along fold line 214 and along an adjacent edge to panel 230 along fold line 225. Removable tab 223 is detachably connected to body portion 221 along arcuate score line 222. Tab 223 has portions 223a and 223b, which are foldably connected to each other along fold line 224. Portion 223a is at least partially defined by the arcuate score line 222 and fold line 224. Portion 223b includes an arcuate cut away portion 225. Tab 223 is adapted to be detached from body portion 221 by ripping along the score line 222.

A third panel 230 includes a body portion 231 which is attached to body portion 221 along fold line 225, and on an opposite edge to body portion 251 of panel 250 along fold line and on an adjacent edge to body portion 241 of a fourth panel 240 along fold line 232.

Body portion 241 includes an angled side 243 with a laterally offset portion 242 which engages slit 212b when the drawer portion 220 is foldably assembled. The inner surface of portion 242 provides an abutment which prevents tab 215 from inadvertently being withdrawn from a folded engagement configuration.

A fifth panel 250 includes a body portion 251 foldably connected to body portion 231 along fold line 233 and to tab 254 by adhesion, or other suitable means of fixation. Body portion 251 includes an arcuate cutaway portion 252 to provide access to the user's finger to grasp and pull the drawer 200. Panel 250 forms an end panel which constitutes side 12 of the dispenser (See FIGS. 3, 4).

A sixth panel 260 includes a body portion 261 which is foldably connected to body portion 271 of panel 270 along fold line 273. Body portion 261 includes a cutaway portion 263 to facilitate grasping of the suture package by the user's finger. Tab 254 of panel 250 is foldably connected to body portion 261 along fold line 262. Fold line 262 is on the edge of panel 250 opposite to that of fold line 233. Body portion 261 included an elongated recess 265 along an edge.

A seventh panel 270 includes body portion 271 attached to body portion 261 along fold line 273, which is adjacent to fold line 262. Body portion 271 also includes an angled edge 274 with a laterally offset portion 272 which engages slit 212a when the drawer portion 220 is foldably assembled. The inner surface of portion 272 provides an abutment which prevents tab 215 from inadvertently being withdrawn from a folded engagement configuration, and acts cooperatively with corresponding lateral offset portion 242 of panel 240.

Figure 8:
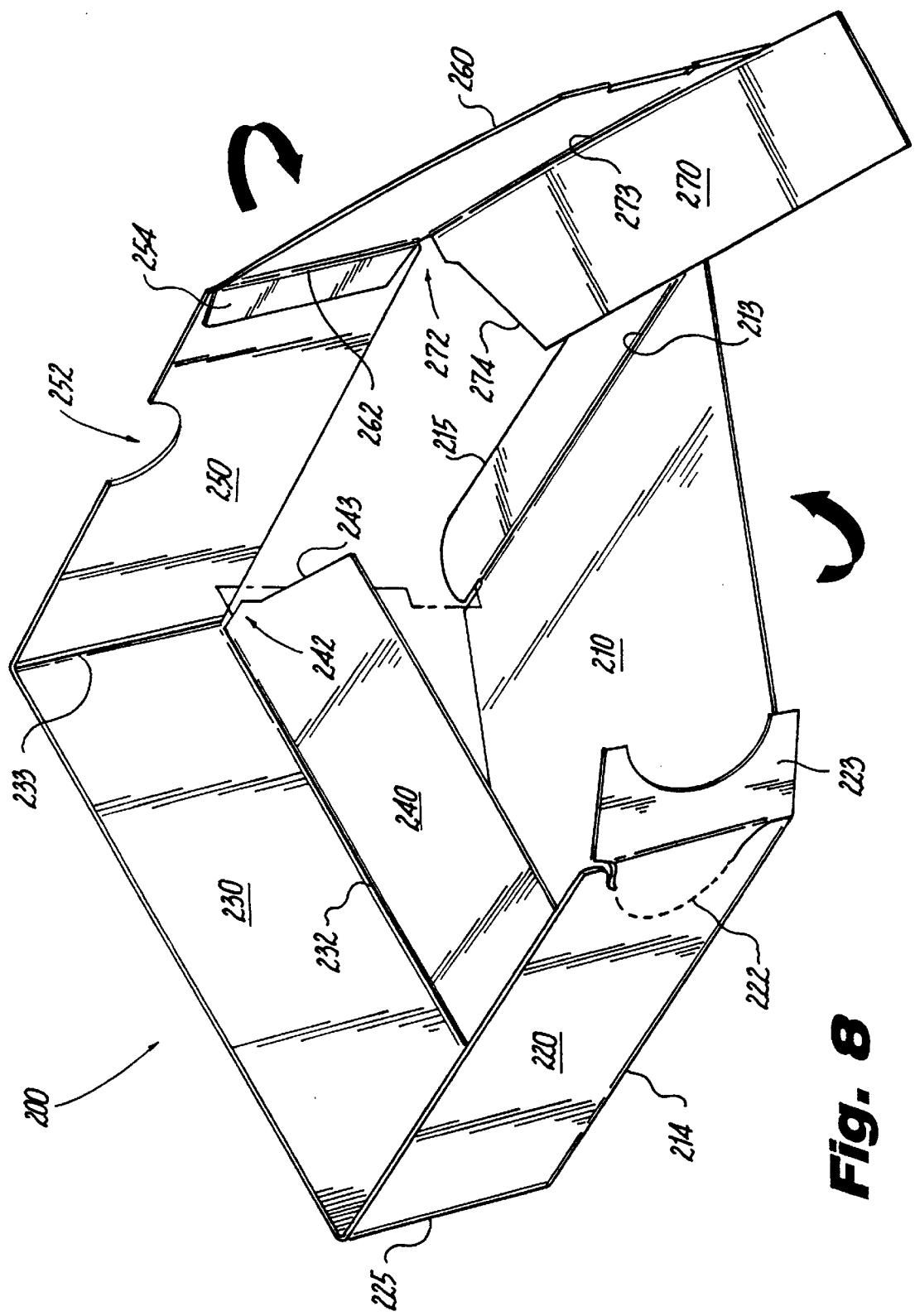
FIG. 8 is a perspective view showing the folding and assembly of the blank of FIG. 7 to form the drawer.
Figure 9:
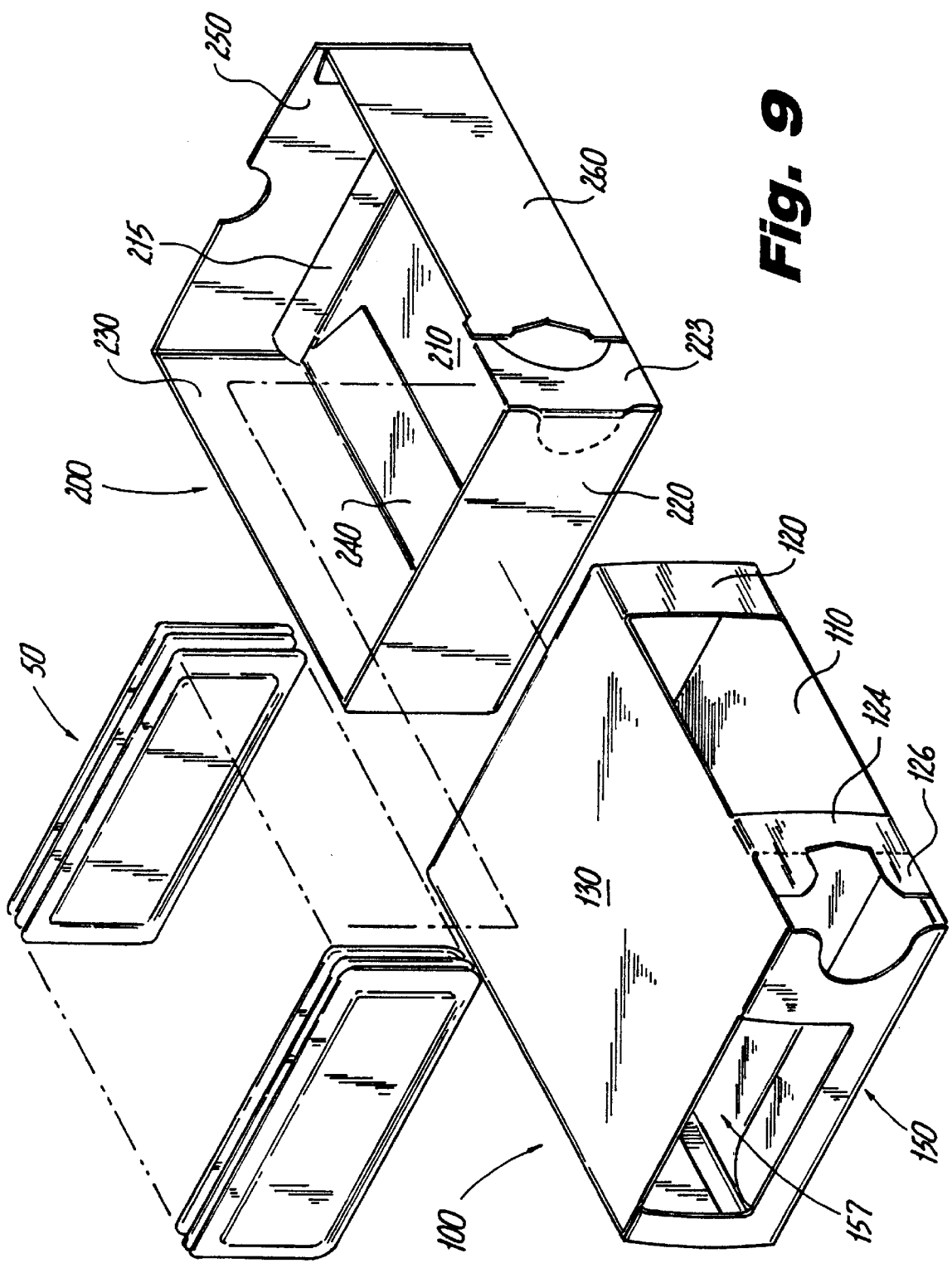
FIG. 9 is an exploded perspective view illustrating the assembly of the drawer and outer casing and the loading of suture packages in the universal dispenser box shown in FIG. 3.

Referring to FIG. 8, the folding assembly of the drawer portion 200 is illustrated. Panels 220, 230, 250, and 260 are folded around along fold lines 225, 233, and 262 to form the sides of the drawer portion 200.

Panels 240 and 270 are then folded up and in along fold lines 232 and 273, respectively. Panel 210, which forms the floor of the drawer portion 200, is then folded up with tab 215 being inserted in the space between body portion 251 and angled edges 243 and 274 of panels 240 and 270, respectively. Lateral offset portions 242 and 272 engage slots 212b and 212a, respectively, thereby retaining the tab 215.

As can be seen from FIGS. 3, 4, 9 and 11, suture package dispenser 10 is a container for holding a plurality of suture packages 50 in a stacked array, the suture packages 50 being of generally planar, rectangular configuration, stacked parallel to each other. The suture package dispenser is characterized by a generally planar first side wall 11 and a generally planar second side wall 12, side walls 11 and 12 being adjacent and substantially perpendicular to each other, and a side wall 13 which constitutes a top panel when the suture dispenser is positioned horizontally on a support surface, as shown in FIG. 4. The first side wall 11 is defined by panel 120 of the outer casing (FIG. 5) in conjunction with panel 260 of the drawer portion (FIGS. 7, 8). Side wall 12 is defined by panel 250 of the drawer portion (FIGS. 7, 8). Side wall 13 is defined by panel 110 (FIGS. 5, 6), and is substantially perpendicular to side walls 11 and 12. The planes of the individual suture packages are oriented perpendicular to the first and third side walls 11 and 13, and parallel to the second side wall 12.

Suture package dispenser 10 includes two access portals through which the suture packages can be individually withdrawn. A first portal 14 is located at the bottom of the first side wall 11 when the suture package dispenser 10 is positioned vertically as shown in FIG. 3.

Referring to FIGS. 3, 9, 10 and 11, removable tab 223 is initially folded over to at least partially close the first portal 14. To withdraw a suture package from the first portal 14 the user detaches tab 223 (FIG. 10), thereby allowing retrieval of a suture package 50.

Figure 11:
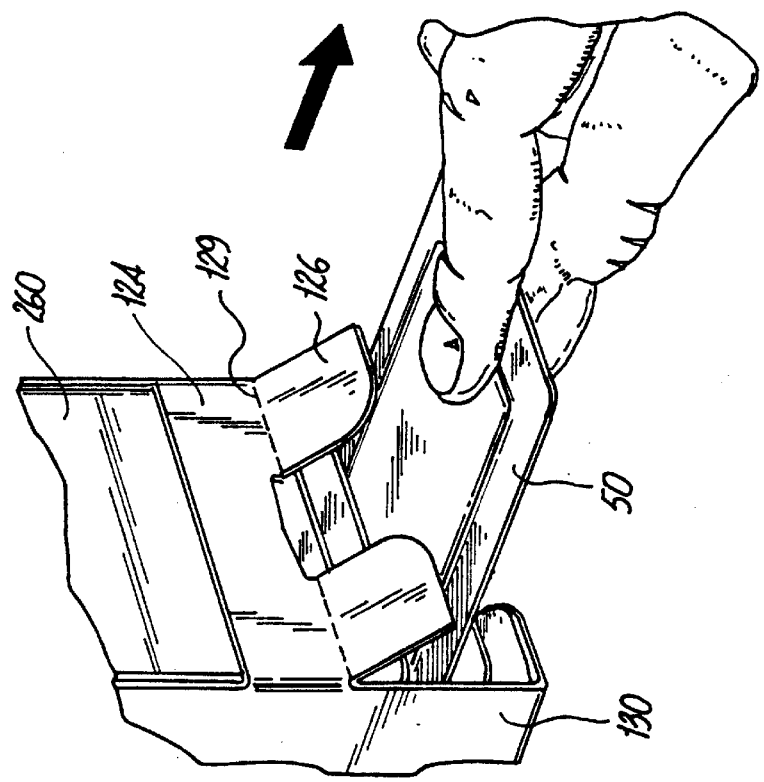
FIG. 11 illustrates dispensing of a suture package.
Figure 10:
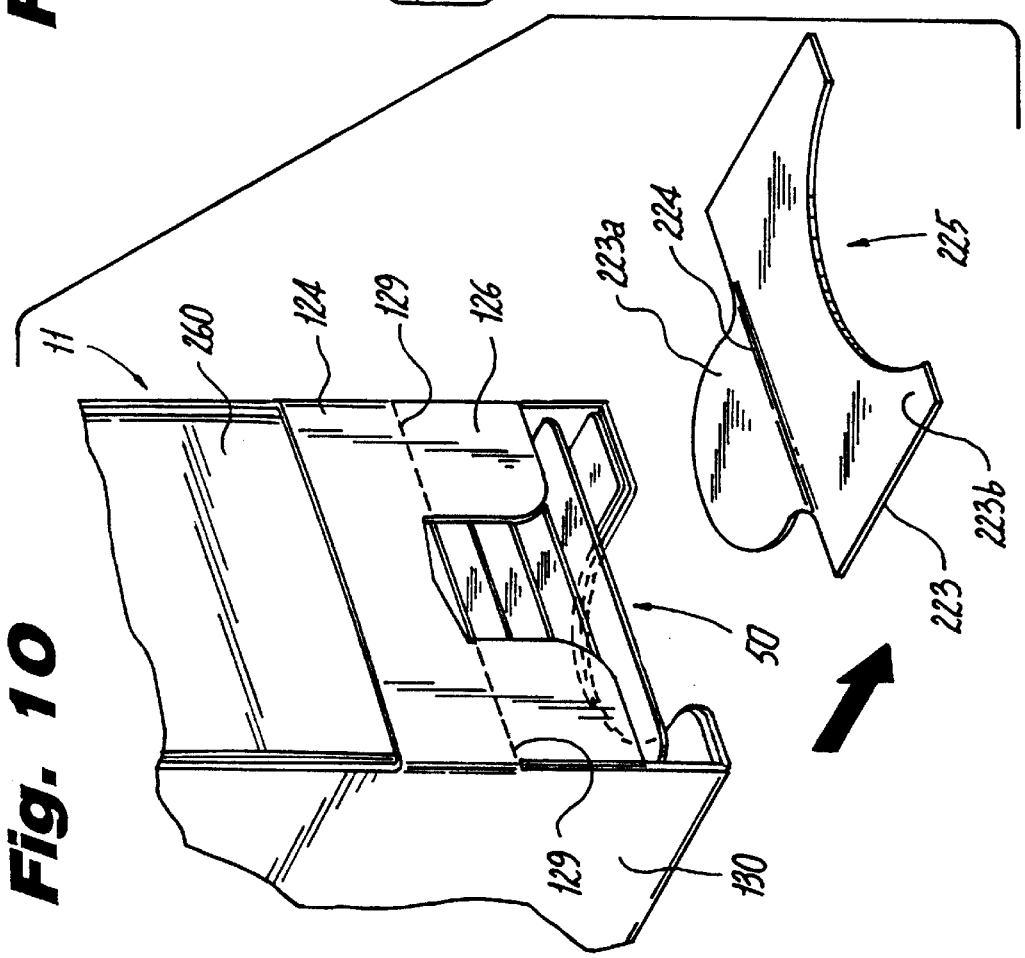
FIG. 10 illustrates the removal of the retainer tab from the universal dispenser box of FIG. 3.

As can be seen in FIG. 11, the suture packages 50 are individually withdrawn through the first portal 14 in a line of direction perpendicular to the first side wall 11 and parallel to both the second side wall 12 and the third side wall 13, as in the U.S. preferred mode of dispensing.

Figure 1:
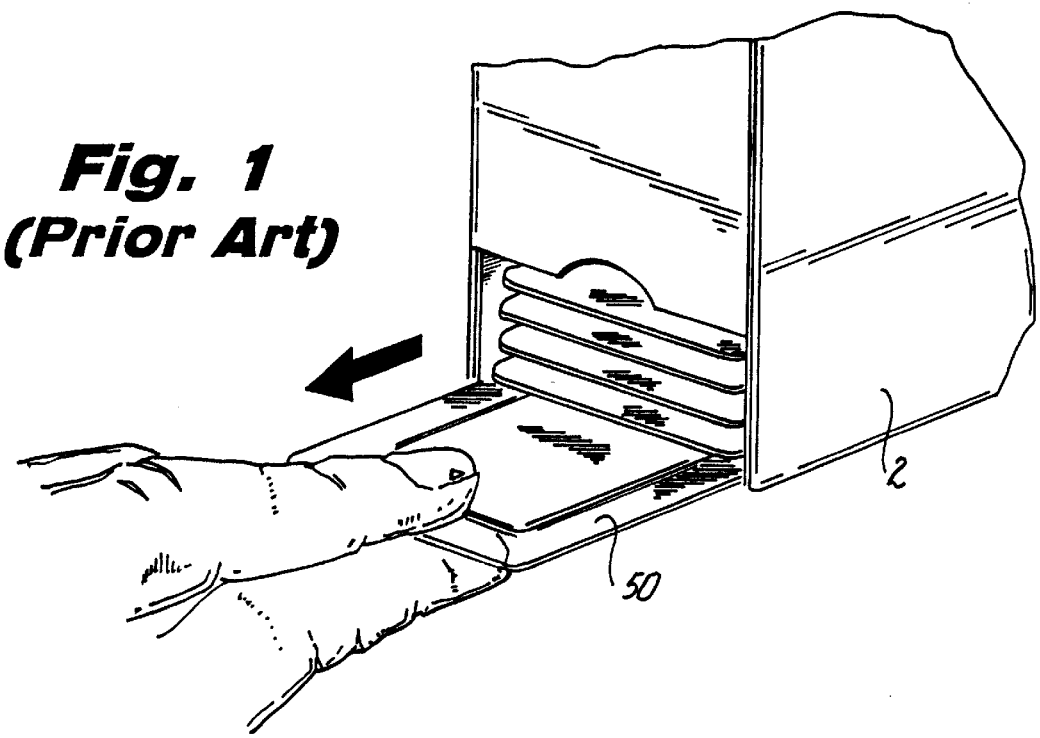
FIGS. 1 and 2 illustrate prior art box containers for dispensing suture packages.
Figure 2:
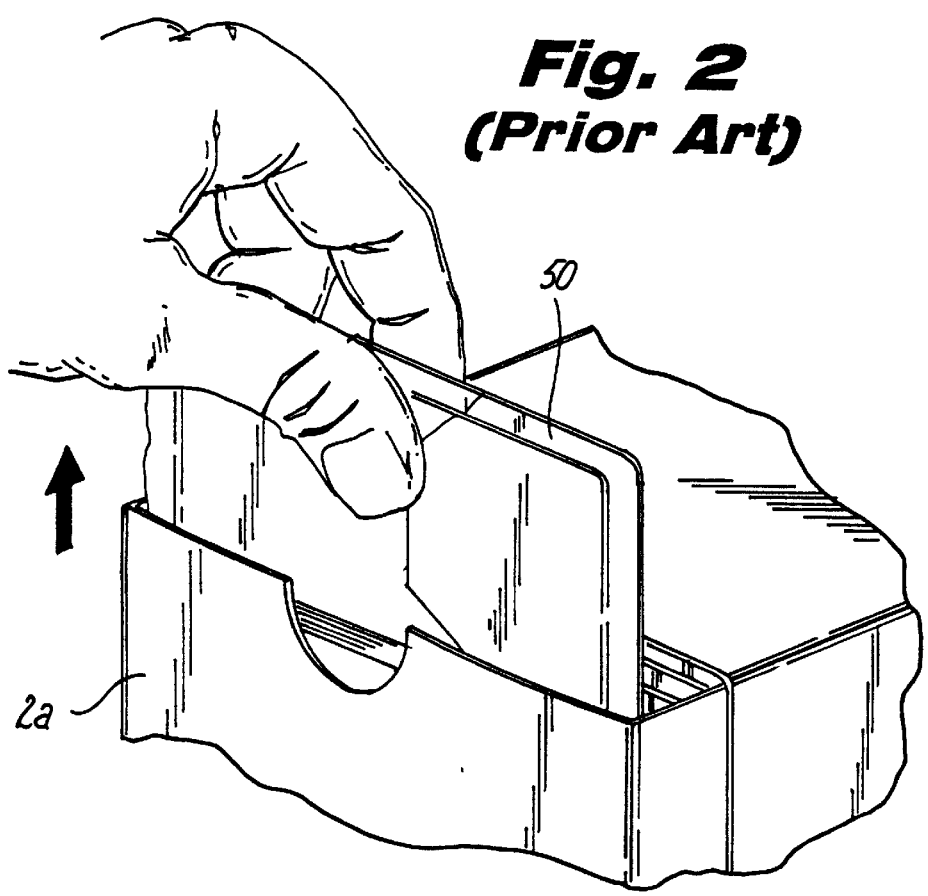

A second portal 15 is defined by side walls 12 and 13. When the drawer portion 200 is fully inserted into the outer casing 100, the second portal 15 is in a closed configuration. When the drawer portion 200 is at least partially withdrawn from the outer casing 100 the second portal 15 is open and a suture package 50 can be removed as in the European preferred mode. See e.g., FIG. 2 which illustrates the European preferred mode of dispensing.

As can be seen, the suture package is removed from the second portal in a line of direction perpendicular to third wall 13, but parallel to both the first side wall 11 and the second side wall 12, although, as mentioned above, the planes of the suture packages are perpendicular to the first side wall 11 and parallel to the second side wall 12.

Figure 12:
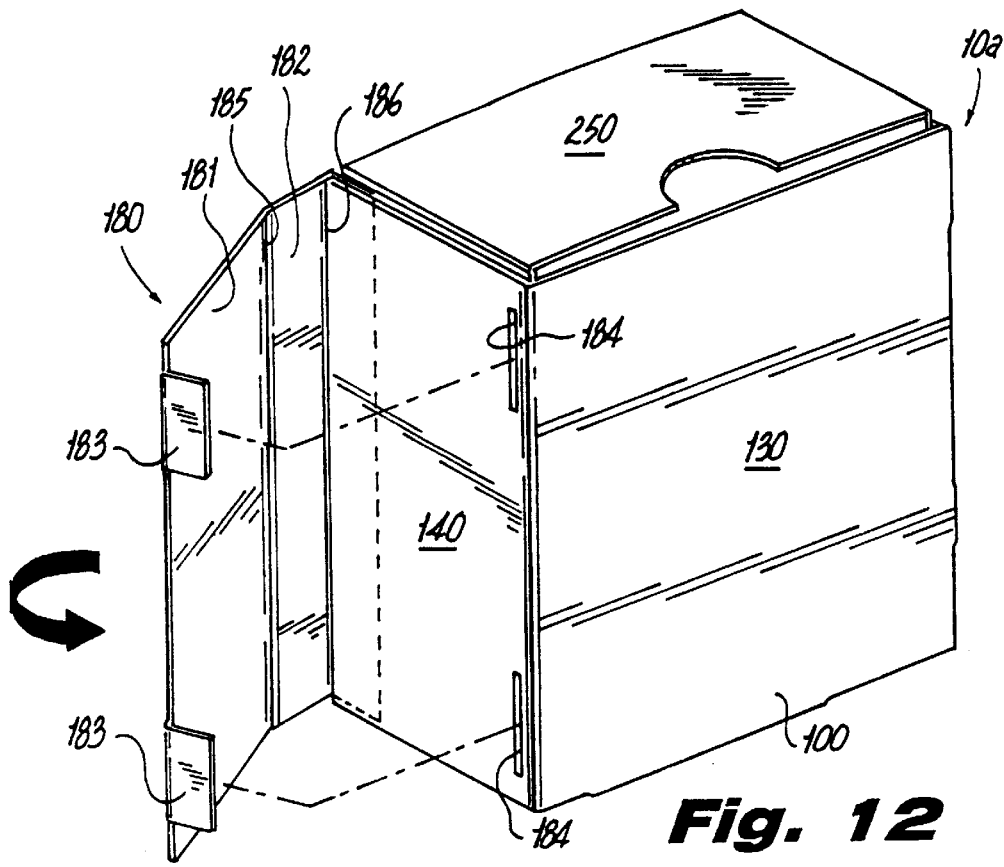
FIG. 12 is a perspective view illustrating of an alternative preferred embodiment including a spacer flap.
Figure 13:
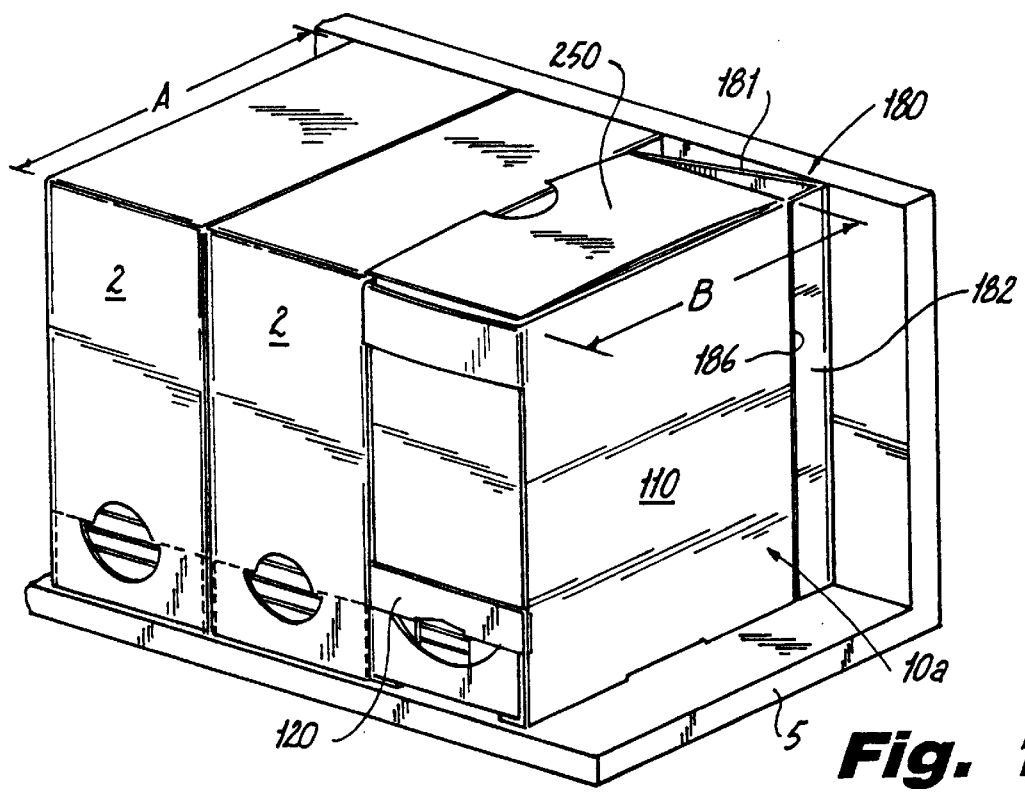
FIG. 13 is a perspective view illustrating the embodiment of FIG. 12 stacked with conventional suture dispenser boxes.

Referring to FIGS. 12 and 13, another embodiment 10a of the universal suture dispenser is shown. In FIG. 13, conventional suture package dispenser boxes 2 are shown oriented vertically for use in the U.S. preferred mode of dispensing. A typical U.S. dispenser box has a depth A, about 5.4 inches. Because the width of the European style box is typically about 4.7 inches (i.e., the length of panel 250 between fold lines 233 and 262, FIG. 7), universal suture package dispenser 10 has a depth B of about 4.7 inches as well. Therefore, when both conventional suture package dispensers 2 and universal suture package dispensers, such as described herein, are shelved together on a U.S. rack 5 there is an uneven presentation because the universal suture dispenser 10 is about 0.7 inches shorter in this dimension. To make up the difference a spacer flap 180 can optionally be included as part of the outer casing 100. Spacer flap 180 includes a main panel portion 181, a spacer panel 182, and insertion tabs 183. The spacer panel 182 is about 0.7 inches wide and makes up for the difference in depth between the universal suture dispenser 10 and conventional suture dispenser boxes 2, as shown in FIG. 13. The spacer panel also causes the dispenser box to properly fit within the U.S. style rack (i.e., the front panel of the box is flush with the front-most portion of the shelving). Spacer panel 182 is preferably fixedly attached to panel 140 of the outer casing. The main panel portion 181 is foldably connected to spacer panel 182 along fold line 185. Tabs 183 extend from the main panel portion 181 and are insertable into slots 184 in the outer casing 100.

For purposes of shipping and for European style dispensing, the spacer flap 180 can be folded back along fold line 186 so that it is flush against panel 110 of the outer casing 100. The user then has the option to bend the spacer flap around to its operating position and insert tabs 183 into slots 184 as shown in FIG. 12, thereby preparing the universal suture package dispenser 10a for shelving with dispenser boxes 2, the U.S. preferred mode.

Figure 14:
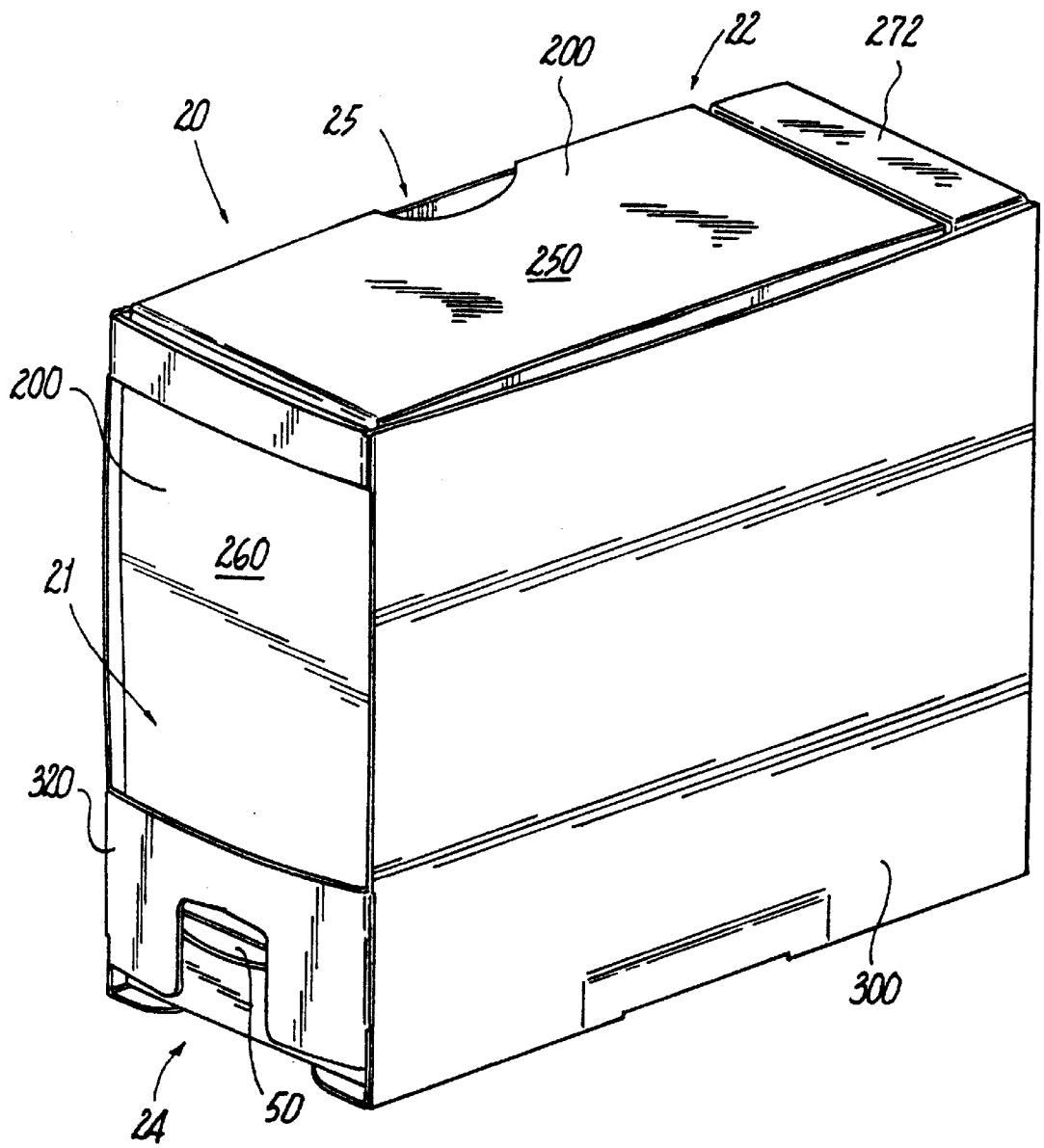
FIG. 14 is a perspective view of an alternative embodiment of the universal suture package dispenser box having a spacer extension wherein the suture packages are stacked vertically.
Figure 15:
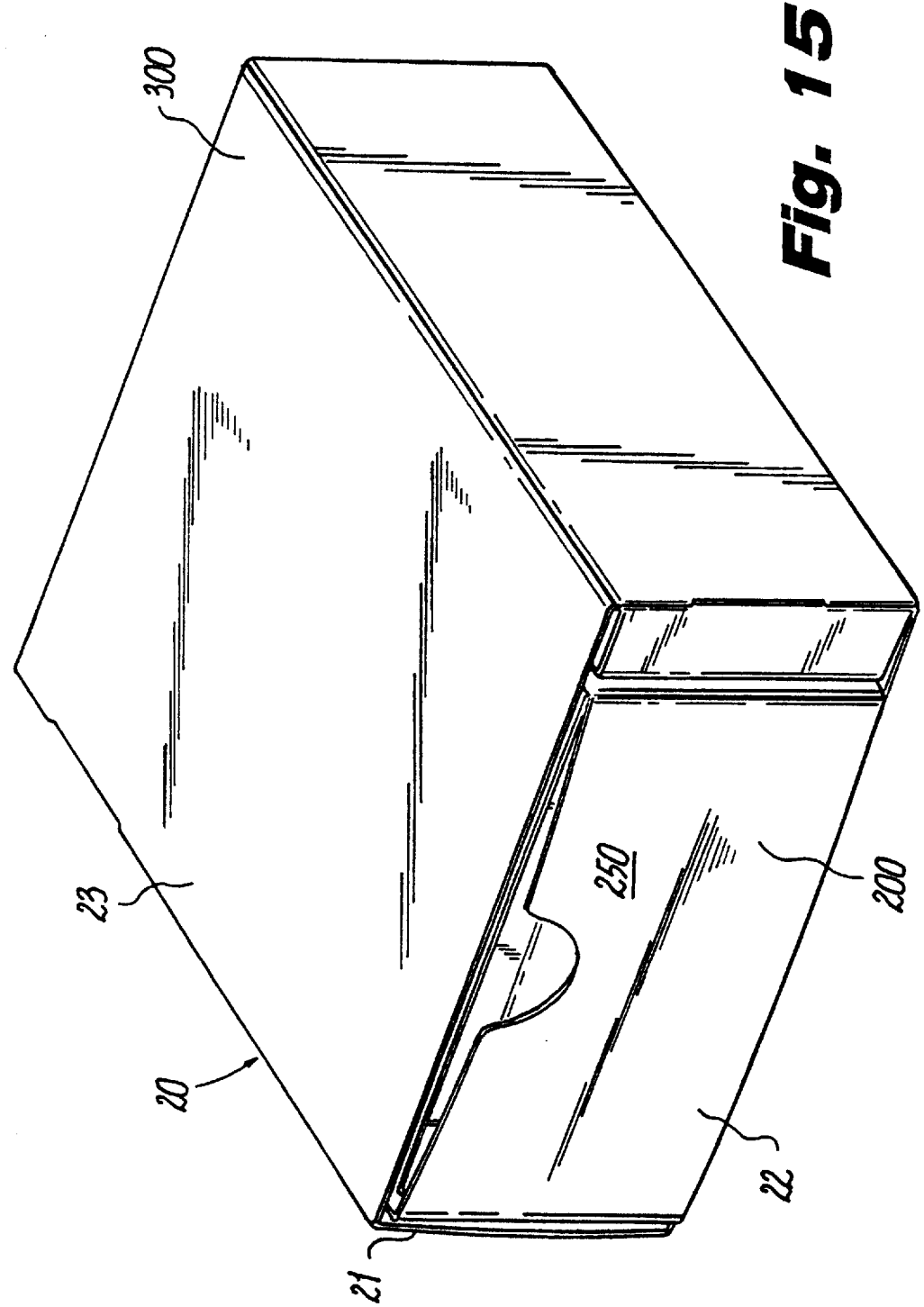
FIG. 15 is a perspective view of the embodiment of FIG. 14 wherein the suture packages are stacked horizontally.

Referring now to FIG. 14, yet another embodiment 20 of the universal suture package dispenser is illustrated in a vertical position as favored in the United States. FIG. 15 illustrates embodiment 20 of the universal suture dispenser positioned in the European preferred horizontal orientation. When universal suture dispenser 20 is used in European style shelving or racks, the outer casing 300 is preferably discarded and drawer 200 is placed in the rack.

Figure 19:
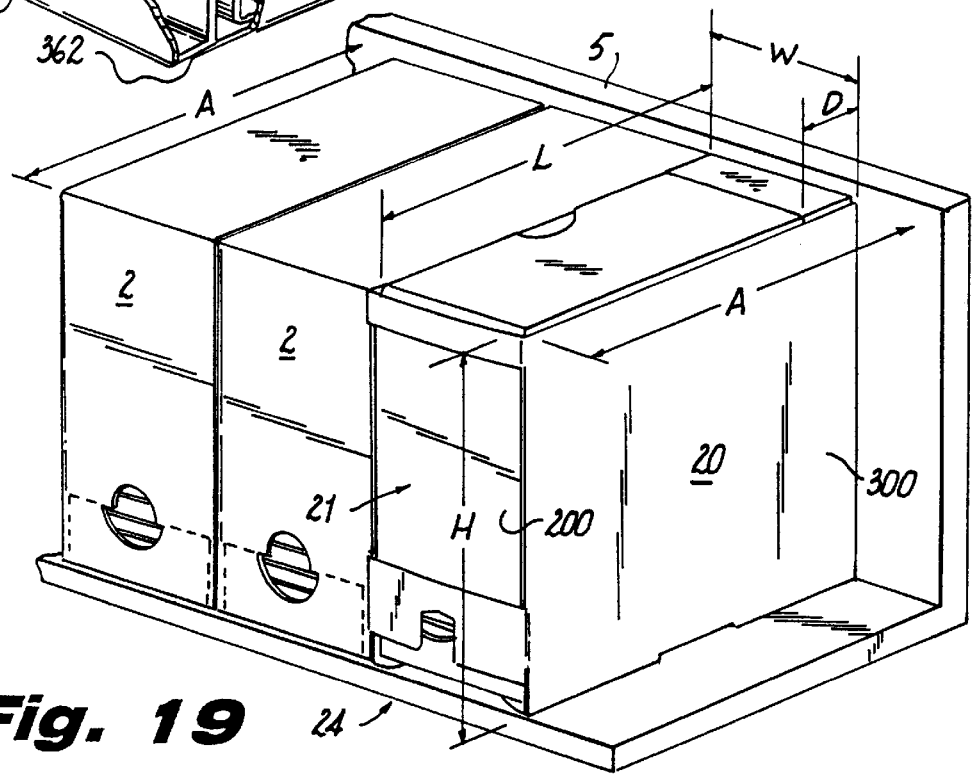
FIG. 19 is a perspective view showing the embodiment of FIG. 14 stacked with conventional suture package dispenser boxes.

Universal dispenser box 20 is provided with a spacer to make up for the difference in dimension between the U.S. and European boxes. Unlike the embodiment shown in FIGS. 12 and 13, the spacer of dispenser box 20 provides a back panel adapted to be completely flush against the rear wall of the U.S. rack on which they are displayed or stored. The universal dispenser box 20 can employ the same drawer portion 200 as that of dispenser box 10. However, the outer casing 300 differs from outer casing 100 by providing a more rigid, permanent spacing member that is oriented inward from the outer periphery of the box rather than outward of the box. More specifically, the outer casing 100 of the embodiment shown in FIGS. 12 and 13 is adapted to fit the drawer portion 200, with additional spacer 180 being provided to adapt the dispenser box 10 to the U.S. rack 5 (FIG. 19). Spacer 180 is exterior to the enclosed space formed by the outer casing 100. Outer casing 300, however, is dimensioned to fit the dispenser box 20 to the rack 5 (FIG. 19), with the spacer portions being provided to adapt the outer casing 300 to the drawer portion 200. The spacer panels are inside an enclosed space defined by the outer casing 300.

Figure 16:
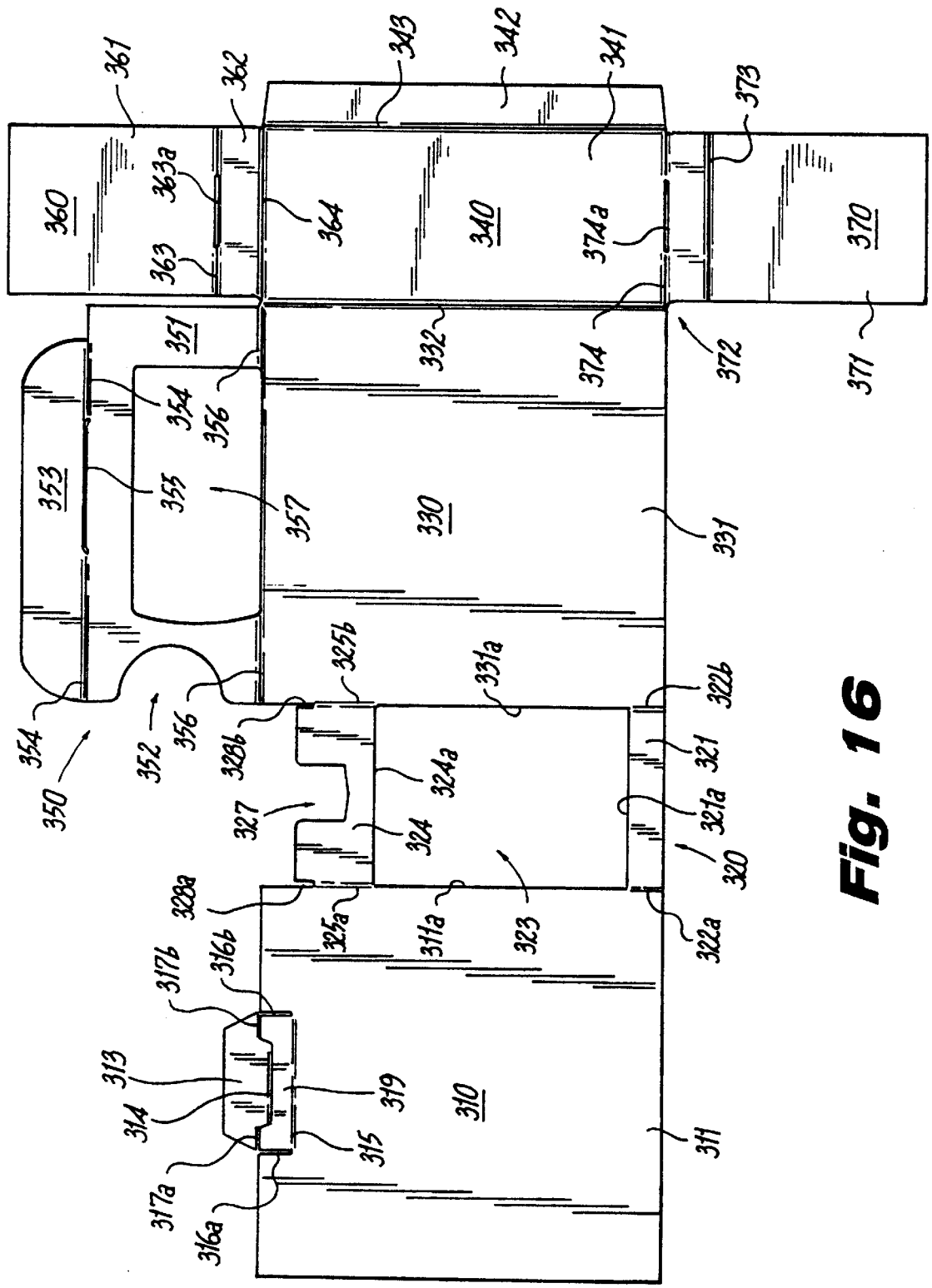
FIG. 16 is a plan view of the blank used to make the outer casing of the embodiment of FIG. 14.

Referring now to FIG. 16, the blank from which the outer casing 300 is made is shown unfolded. The blank has five main panels which correspond to exterior sides of the outer casing, and spacer panels to adapt the interior dimensions of the enclosed space to fit the drawer portion 200. Each of the panels is a flat sheet of suitable material.

Panel 310 has a body portion 311 and tab 313. Tab 313 is adapted for insertion into slot 355 (discussed below) and is attached to bendable portion 319 along fold line 314. Bendable portion 319 is at least partially defined by slots 316a and 316b, and is attached to body portion 311 along fold line 315. Slots 317a and 317b between tab 313 and bendable portion 319 facilitate the bending of tab 313 relative to the bendable portion 319 and help to prevent inadvertent withdrawal of tab 313 from slot 355 after they have been fully engaged.

Panel 320 includes a first strip portion 321 extending between panels 310 and 330 and which is foldably connected thereto along fold lines 322a and 322b, respectively. A second strip portion 324 extends between panels 310 and 330 and is foldably connected thereto along fold lines 325a and 325b. Edges 311a of the panel 310, 331a of panel 330, 324a of strip 324, and 321a of strip 321 define a window 323. Window 323 enables the operating room personnel or other user to see identifying indicia printed on the outer side of panel 260 of the drawer portion 200 when the dispenser is assembled. Finger slot 327 provides access to grasp the suture package with one's fingers (usually forefinger and thumb).

Panel 330 includes a body portion 331 attached to first and second strip portions 321 and 324 along fold lines 322b and 325b, respectively, and further is attached to panel 340 along fold line 332.

Panel 340 includes a body portion 341 to which flap 342 is attached along fold line 343.

Panel 350 includes a body portion 351 attached to panel 330 along fold line 356 and also includes a window 357 for permitting the operating room personnel or other user to read identifying indicia on the outer surface of panel 220 of the drawer portion 200.

Panel 350 also preferably includes an arcuate cut out portion 352 to facilitate grasping of the suture package for withdrawal. Tab 353 is bendably attached to body portion 351 along fold line 354. Slot 355 is disposed along fold line 354 and is adapted to receive tab 313 of the first panel when the panels are folded together to form the outer casing.

Spacer panel 360 includes a body portion 361 and a spacer portion 362 which is attached to body portion 361 along fold line 363. Fold line 363 can include a slit 363a extending partially across the fold line. Spacer portion 362 is attached to one edge of body portion 341 along fold line 364.

Spacer panel 370 includes a body portion 371 and a spacer portion 372 which is attached to body portion 371 along fold line 373. Spacer portion 372 is attached to an edge of the body portion 341 along fold line 374. Fold line 374 can include a slit 374a extending partially across the fold line.

Figure 17:
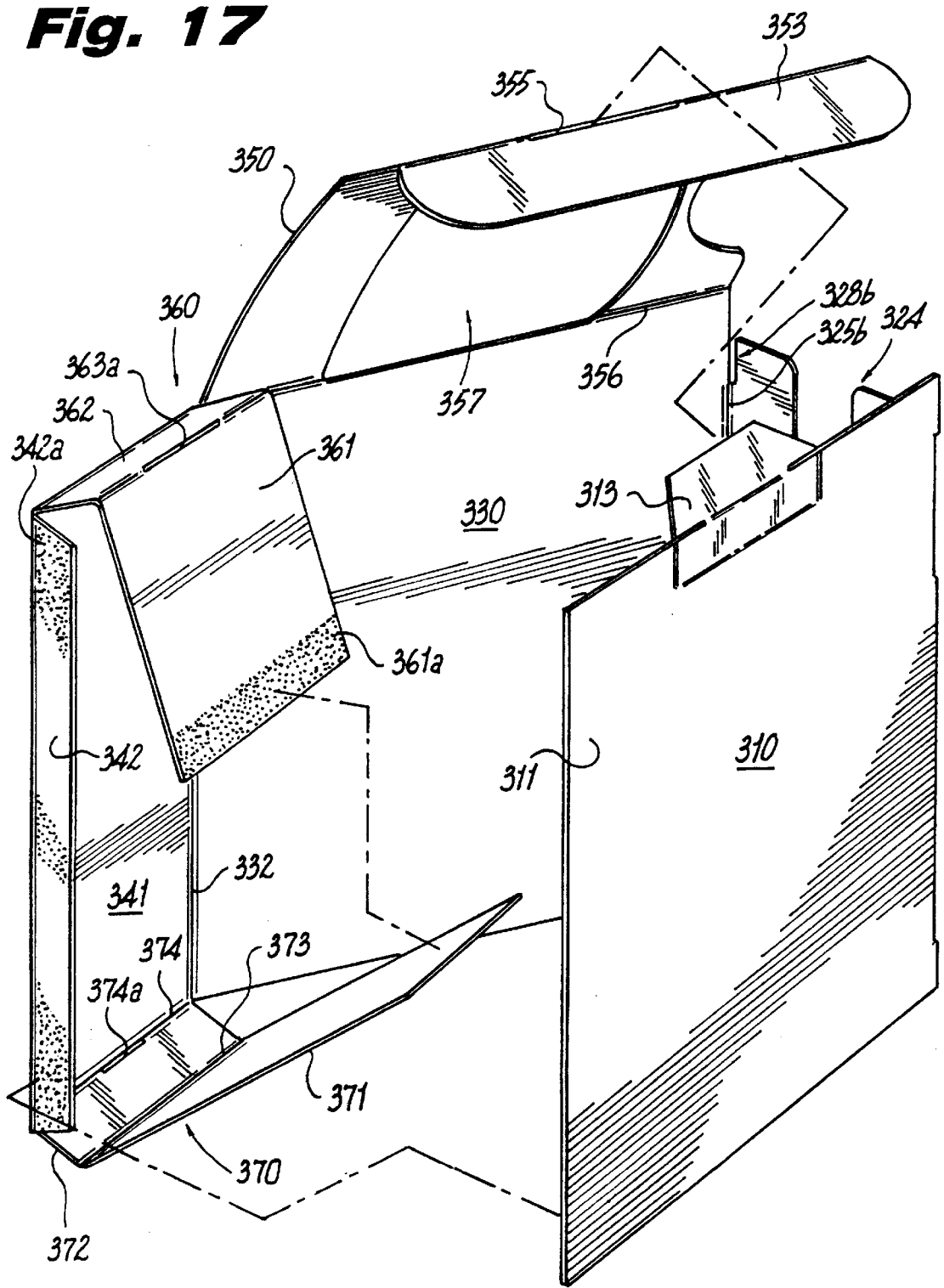
FIG. 17 is a perspective view illustrating the folding and assembly of the blank of FIG. 16.

Referring now to FIG. 17, the folding operation is illustrated. Panels 310, 320, 330, 340, and 350 are folded inward along fold lines 322a, 325a, 322b, 325b, 332, and 356 to form a box-like structure. Tab 342 includes a gummed adhesive surface 342a adapted to abut an inner surface portion of panel 310 and to adhere thereto. Panel 350 is folded with tab 353 tucked inside panel 310 with tab 313 being inserted through slot 355 to lock the panels and secure the enclosure. The spacer panels 360 and 370 are folded along fold lines 363, 364, 373, and 374 to construct an interior wall (formed by body portions 361 and 371) parallel to and spaced apart from body portion 341 by a distance equal to the width of spacer portions 362 and 372. Body portion 361 can have a gummed surface portion 361a to adhere to body portion 371. The outer casing thus formed is prepared to receive the drawer portion 200.

Figure 18:
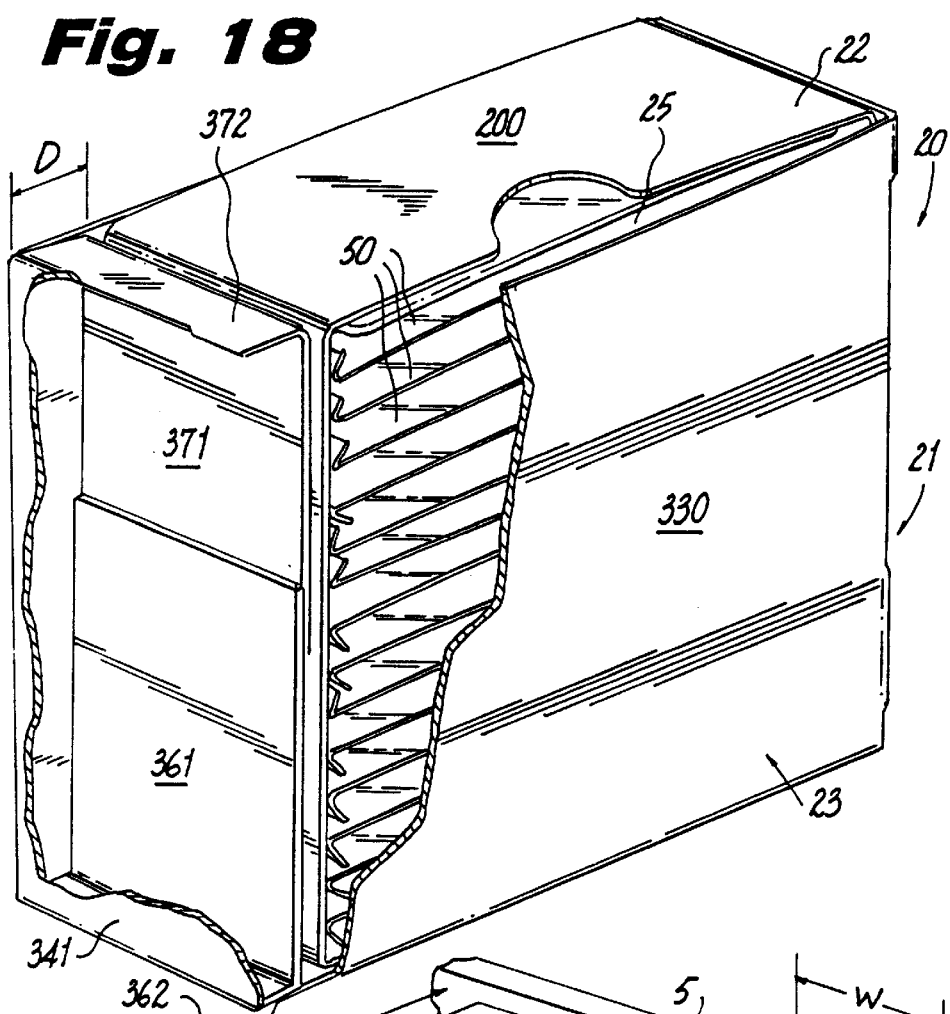
FIG. 18 is a cutaway view of the embodiment of FIG. 14.

Referring now to FIGS. 18 and 19, it can be seen that the outer casing 300 is adapted to correspond in dimensions to U.S. prior art suture package dispensers 2 so that suture package dispenser box 20 can be shelved alone or side by side with the conventional boxes 2 on a standardized U.S. display or storage rack 5 to present a uniform array of dispenser boxes flush with the front of the shelving. Both the prior art suture package dispensers 2 and the outer casing 300 of the suture dispenser 20 are characterized by a depth dimension A. However, the drawer portion 200 is characterized by a dimension L which is less than A. It is this dimension, L, that corresponds to the preferred European width for a suture dispensing box. Spacer panels 360 and 370 provide an interior wall formed by body portions 361 and 371, which is spaced apart from exterior panel 341 by a distance D equal to the width of spacer portions 362 and 372. Width D is chosen such that the dimensions of the drawer portion 200 are accommodated within the outer casing 300, as previously explained. Most preferably, with respect to FIG. 19, dimension A is about 5.4 inches, spacer width D is about 0.7 inches, height H is about 5.6 inches and box width W is about 2.5 inches. Therefore, the exterior dimensions of the U.S. preferred suture dispensing box is about 2.5×5.6×5.4 inches, while the European suture package dispenser drawer is about 2.5×5.6×4.7 inches (±about 0.5 inches in each dimension).

In like manner as with suture package dispenser 10, and as can be seen from FIGS. 14, 15, and 19, the suture package dispenser 20 includes a container for holding a plurality of suture packages 50 in a stacked array, the suture packages 50 being of generally planar configuration, stacked parallel to each other. The suture package dispenser 20 is characterized by a generally planar first side wall 21 and a generally planar second side wall 22, side walls 21 and 22 being adjacent and substantially perpendicular to each other, and a side wall 23 which constitutes a top panel when the suture dispenser is positioned horizontally on a support surface, as shown in FIG. 15. The first side wall 21 is defined by panel 320 of the outer casing (FIG. 16) in conjunction with panel 260 of the drawer portion (FIGS. 7, 8). Second side wall 22 is defined by panel 250 of the drawer portion (FIGS. 7, 8). Side wall 23 is defined by panel 310 (FIGS. 16, 17), and is substantially perpendicular to side walls 21 and 22. The planes of the individual suture packages are oriented perpendicular to the first and third side walls 21 and 23, and parallel to the second side wall 22.

Suture package dispenser 20 includes two access portals through which the suture packages 50 can be individually withdrawn. A first portal 24 is located at the bottom of the first side wall 21 when the suture package dispenser 20 is positioned vertically (U.S. preferred mode) as shown in FIG. 14.

Removable tab 223 is initially folded over to at least partially close the first portal 24. To withdraw a suture package from the first portal 24 the user detaches tab 223, thereby allowing retrieval of a suture package 50. The suture packages 50 are withdrawn (by grasping a shorter side of the rectangular suture package) through the first portal 24 in a line of direction perpendicular to the first side wall 21 and parallel to both the second side wall 22 and the third side wall 23, as in the U.S. preferred mode of dispensing.

The second portal 25 is defined by side walls 22 and 23. When the drawer portion 200 is fully inserted into the outer casing 300, the second portal 25 is in a closed configuration. When the drawer portion 200 is at least partially withdrawn from the outer casing 300 the second portal 25 is open and a suture package 50 can be removed (by grasping a longer side of the rectangular suture package) as in the European preferred mode. As discussed above, drawer 200 can be removed from casing 300 and placed alone in a dispensing rack.

As can be seen, the suture package is removed from the second portal 25 in a line of direction which is perpendicular to third wall 23, but parallel to both the first side wall 21 and the second side wall 22, although, as mentioned above, the planes of the suture packages are perpendicular to the first side wall 21 and parallel to the second side wall 22.

It can further be seen from FIG. 18 that the interior wall formed by body portions 361 and 371 of the spacer panels 360 and 370 is oriented in a plane which is parallel to first side wall 21.

It will be understood that various modifications may be made to the embodiments described herein. Therefore the above description should not be construed as limiting, but merely as exemplifications of preferred embodiments. Those skilled in the art will envision other modifications within the scope and spirit of the claims appended hereto.

What is claimed is:

1. A suture package dispenser comprising:

a container for holding a plurality of suture packages in a stacked array, the suture packages being of generally planar configuration and stacked such that the planes of the packages are parallel to each other;

the container having a first side wall generally defining a first plane and a second side wall adjacent to the first side wall and generally defining a second plane oriented substantially perpendicular to the first plane, wherein the individual suture package planes are oriented perpendicular to the first plane and parallel to the second plane; and, the container having a first access portal and a second access portal for withdrawal of the suture packages from the stacked array, the first access portal permitting the suture packages to be withdrawn from the container in a line of direction perpendicular to the first plane and parallel to the second plane, and the second access portal permitting the suture packages to be withdrawn from the container in a direction parallel to both the first and second planes, wherein the container includes an outer casing and a drawer portion slidably disposed within the outer casing and linearly movable in a direction perpendicular to the second plane.

2. The suture package dispenser of claim 1 wherein the drawer portion has a storage space for holding the stacked array of suture packages.

3. The suture package dispenser of claim 2 wherein the first access portal is positioned on the first side of the container and is at least partially defined by corresponding openings in the drawer portion and the outer casing.

4. The suture package dispenser of claim 3 wherein the opening in the drawer portion is at least partially formed by removal of a tab which is removably attached to the drawer portion.

5. The suture package dispenser of claim 4, wherein the second side of the container is defined by an end panel of the drawer portion, the outer casing having a first side wall which is adjacent and substantially perpendicular to the first and second sides of the container, and the second portal is at least partially defined by the end of the drawer portion and the first side wall of the outer casing, the second portal being in an open configuration when the drawer portion is at least partially withdrawn from the outer casing and in a closed configuration when the drawer portion is fully disposed within the outer casing.

6. The suture package dispenser of claim 1 wherein the container is fabricated from a material selected from the group consisting of paperboard and plastic sheet.

7. The suture package dispenser of claim 1 wherein the container includes a window for viewing the suture package at one end of the stacked array.

8. The suture package dispenser of claim 1 further including a spacer flap foldably connected at one edge to the outer casing, the spacer flap including at least one tab for insertion within a corresponding slot in the outer casing.

9. The suture package dispenser of claim 1 wherein the drawer portion has at least one side dimension which is less than a corresponding side dimension of the outer casing, and the outer casing includes at least one spacer panel spaced apart from an exterior wall of the outer casing by a distance substantially equal to the difference between the corresponding side dimensions of the outer casing and drawer portion, and which is oriented parallel to said first plane.

10. A suture package dispenser comprising:

a) an outer casing which includes an outer casing first panel, an outer casing second panel foldably connected to the outer casing first panel along an edge thereof, an outer casing third panel foldably connected to the outer casing second panel on an edge of the outer casing second panel opposite to the edge at which the outer casing first panel is foldably connected, an outer casing fourth panel foldably connected to the outer casing third panel along an edge of the outer casing third panel opposite to that at which the outer casing second panel is connected, and an outer casing fifth panel foldably connected to the outer casing third panel; said outer casing first, second, third, fourth and fifth panels forming at least a partial enclosure defining an interior space and having an open end;

b) a drawer portion slidably disposed within the interior space of the outer casing and at least partially withdrawable through the open end of the outer casing, the drawer portion including drawer portion first, second, third, fourth, fifth, sixth, and seventh panels, the drawer portion first and third panels being foldably connected to the drawer portion second panel along respective adjacent edges of the drawer portion second panel, the drawer portion fifth and fourth panels being foldably connected to the drawer portion third panel along respective adjacent edges of the drawer portion third panel, and the drawer portion fifth and seventh panels being foldably connected to the drawer portion sixth panel along respective adjacent edges of the drawer portion sixth panel, the drawer portion first, second, third, fourth, fifth, sixth, and seventh panels being folded to form a storage space for suture packages.

11. The suture package dispenser of claim 10 wherein the outer casing second panel and the outer casing fifth panel each have a window.

12. The suture package dispenser of claim 10 wherein the outer casing first panel includes a tab and the outer casing fifth panel includes a slot into which the tab is inserted.

13. The suture package dispenser of claim 10 wherein the drawer portion second panel includes a tab removably attached to the drawer portion second panel along an arcuate score line.

14. The suture package dispenser of claim 10 wherein the drawer portion fifth panel and drawer portion second panel are foldably attached to opposite edges of the drawer portion third panel.

15. The suture package dispenser of claim 14 wherein the drawer portion sixth panel and drawer portion third panel are foldably attached to opposite edges of the drawer portion fifth panel.

16. The suture package dispenser of claim 10 wherein said outer casing and drawer portion are fabricated from a material selected from the group consisting of paperboard and plastic sheet.

17. The suture package dispenser of claim 10 further including a plurality of substantially planar suture packages stacked in an array such that the suture packages are parallel to each other and parallel to the drawer portion second and fifth panels.

18. The suture package dispenser of claim 17 further including first and second access portals for withdrawal of the suture packages, the first access portal permitting the suture packages to be withdrawn from the dispenser in a linear direction perpendicular to the outer casing second panel, and the second access portal permitting withdrawal of the suture packages in a line of direction perpendicular to the outer casing first panel.

19. A method of presenting suture packages comprising:
  providing a plurality of suture packages, the suture packages being generally planar and rectangular in shape and having first and second sides, the first side being longer than the second side;
  providing a drawer for receiving the suture packages, the drawer having first and second separate access areas for removing suture packages therefrom, the first access area permitting removal of a suture package in a first linear direction substantially parallel to the plane of the suture package, and the second access area permitting removal of a suture package in a second linear direction substantially parallel to the plane of the suture package but substantially perpendicular to the first linear direction;
  disposing a plurality of the suture packages in the drawer; and
  removing a suture package from the drawer, wherein the step of removing the suture package is performed by either grasping the first long side of the suture package and removing the suture package through the first access area or by grasping the second, short side of the suture package and removing the suture package through the second access area.

20. The method according to claim 19, further comprising the steps of providing a casing adapted to slidably receive the drawer and sliding the drawer into the casing.

21. The method according to claim 20, wherein the step of providing the casing comprises providing a casing having a side wall with an opening such that the second access area of the drawer is aligned with the casing side wall opening when the drawer is slid into the casing, thereby providing access to the short sides of the suture packages through both the casing and the drawer.

* * * * *